United States Patent [19]

Pannell

[11] Patent Number: 5,667,518
[45] Date of Patent: Sep. 16, 1997

[54] METHOD AND IMPLEMENTS FOR PERFORMING A VASECTOMY

[76] Inventor: William P. Pannell, 177 Wiley Acres Rd., Cordele, Ga. 31015

[21] Appl. No.: 538,045

[22] Filed: Oct. 2, 1995

[51] Int. Cl.$^6$ ............................................. A61B 17/08
[52] U.S. Cl. .................................. 606/151; 606/222
[58] Field of Search .................................. 128/843, 898; 606/151, 157, 222, 223

[56] References Cited

U.S. PATENT DOCUMENTS

| | | |
|---|---|---|
| 1,192,596 | 7/1916 | Albrecht . |
| 2,097,039 | 10/1937 | Peterson . |
| 2,634,726 | 4/1953 | Hanson ............................ 128/221 |
| 3,509,880 | 5/1970 | Guttman . |
| 3,547,124 | 12/1970 | Ferqusson . |
| 3,716,056 | 2/1973 | Brodsky et al. ............ 128/303 R |
| 3,941,121 | 3/1976 | Olinger et al. ..................... 128/6 |
| 4,380,238 | 4/1983 | Colucci et al. . |
| 4,390,019 | 6/1983 | LeVeen et al. . |
| 4,413,993 | 11/1983 | Guttman . |
| 4,449,531 | 5/1984 | Cerwin et al. . |
| 4,487,205 | 12/1984 | DiGiovanni et al. . |
| 4,498,476 | 2/1985 | Cerwin et al. . |
| 4,506,671 | 3/1985 | Green . |
| 4,551,888 | 11/1985 | Beecher ............................ 24/30 |
| 4,667,671 | 5/1987 | Danzig . |
| 4,682,598 | 7/1987 | Beraha ............................ 128/305 |
| 4,710,180 | 12/1987 | Johson . |
| 4,733,666 | 3/1988 | Mercer, Jr. ...................... 128/346 |
| 4,800,879 | 1/1989 | Golyakhovsky et al. . |
| 4,917,677 | 4/1990 | McCarthy ........................ 606/151 |
| 4,957,502 | 9/1990 | Takase ............................ 606/223 |
| 4,967,949 | 11/1990 | Sandhaus ........................ 227/176 |
| 4,976,722 | 12/1990 | Failla ............................... 606/157 |
| 5,219,353 | 6/1993 | Garvey, III et al. ............ 606/157 |
| 5,269,792 | 12/1993 | Kovac et al. ................... 606/158 |
| 5,281,228 | 1/1994 | Wolfson . |
| 5,531,761 | 7/1996 | Yoon ............................... 606/223 |

Primary Examiner—Michael Buiz
Assistant Examiner—Tina T. D. Pham
Attorney, Agent, or Firm—Finnegan, Henderson, Farabow, Garrett & Dunner

[57] ABSTRACT

A safe and effective method of performing a vasectomy with minimal patient discomfort involves manipulating the vas deferens to a forward, operative position adjacent the scrotal wall where a hypodermic needle is inserted to isolate the vas deferens thereat and to administer a local anesthetic through side-opening injection ports. A crescent-shaped surgical slip is then applied with the needle in place, to tightly clamp the vas deferens between a folded portion of the scrotal skin. The portions of the scrotal skin and vas deferens forward of the clip are then excised.

9 Claims, 4 Drawing Sheets

METHOD AND IMPLEMENTS FOR PERFORMING A VASECTOMY

BACKGROUND OF THE INVENTION

1. Field of the Invention

The present invention relates to surgical procedures, in general. More particularly, the present invention relates to vasectomies.

2. Description of the Related Art

Birth control measures that are currently being used are considered pre-conceptive, because each method is directed toward the prevention of the union of the spermatozoa and the ovum. The exception is the use of intra-uterine devices that prevent the implantation of the fertilized ovum. Other mechanical devices such as condoms and diaphragms are pre-conceptive in their function and have been used successfully for many years. Hormonal manipulation in the female can prevent ovulation and has been used extensively over the past forty years.

The major advantage of mechanical devices and pharmacologically controlled menses relates to the temporary suspension of normal conception. No permanent sterility is produced, and pregnancy can be planned. The disadvantages involve varying degrees of effectiveness, the need for regular compliance, and the occasional complications associated with exogenous hormone ingestion.

The surgical procedures that remove the germ cell organs of reproduction, bilateral orchiectomies in the male and bilateral oophorectomies in the female, have never been considered as reasonable birth control measures because of the extensiveness of the surgical procedures and the sudden hormone withdrawal. Hysterectomies, the removal of the uterus, are similarly considered a radical approach to birth control. The surgical approach to birth control has focused primarily on the disruption or occlusion of the tubules through which the sperm and the ovum pass. Tubal ligations in the female require an opening into the peritoneal cavity and use of a general or regional anesthetic in a hospital environment. Vasectomies in the male utilize a direct approach through the scrotum and can be effected with a local anesthetic in a physicians office.

Ligation of these ducts—oviducts in the female and vas deferens in the male—is very effective in preventing pregnancy. Although both procedures may be reversed, they involve very complicated and specialized surgical procedures that are often not successful in reestablishing the ducts. Patients undergoing these procedures must realize that the inducted sterility is often irreversible.

Ideally a vasectomy is an outpatient procedure that is quickly completed with minimal discomfort for the patient. He should then immediately be capable of resuming his normal activities. The majority of cases have this degree of successful results and minimal aftereffects. However, in a significant number of instances, prolonged exploration and manipulation accompanied by excessive discomfort both intraoperatively and postoperatively can make the results less than desirable.

Current vasectomy procedures involve the injection of a local anesthetic into the scrotal skin and then into the area surrounding the vas deferens. One or two incisions are then made and the vas is dissected, free to be ligated and divided. The scrotal openings then may or may not be closed with a suture. The manner in which the tissue is handled determines the amount of postoperative swelling and subsequent pain. Consideration of less than desirable results focuses attention on two important points. First, scrotal tissue is elastic and does not provide the benefits of tamponade found in many other parts of the body. In less compliant skin and soft tissue, tight closure of the incision minimizes postoperative bleeding and swelling. The scrotal skin and soft tissue offer little pressure to slow the loss of blood and fluid. Besides causing discomfort, the healing process is slowed because of the prolonged time required to reabsorb these fluids and cells, increasing the opportunity for bacterial colonization.

Another concern for the surgeon is the elusiveness of the vas deferens. This structure cannot be seen until the later stages of the procedure and must be identified by palpation. Once identified and delivered up to the scrotal opening, it must be held in place by some means of fixation. Even a momentary release of the vas allows it to immediately return to within the spermatic cord, from which it must again be extricated. The injection of a local anesthetic into the scrotal skin and the area surrounding the vas makes palpation of the structure difficult. Loss of fixation of the vas results in the need for increased dissection and manipulation causes increased bleeding and swelling.

SUMMARY OF THE INVENTION

Accordingly, the present invention is directed to a method of performing a vasectomy and associated vasectomy implements that substantially obviate one or more of the limitations and disadvantages of the related art.

Additional features and advantages of the invention will be set forth in the description which follows or may be learned by practice of the invention. The objectives and other advantages of the invention will be realized and attained by the method and apparatus particularly pointed out in the written description and claims hereof, as well as the appended drawings.

To achieve these and other advantages, and in accordance with the purpose of the invention, as embodied and broadly described, the invention resides in a method of performing a vasectomy that comprises the steps of identifying the vas deferens from the spermatic cord by digital palpation; manoeuvering the vas deferens to an operative position adjacent a wall of the scrotal sac; inserting a hypodermic needle through a folded portion of the scrotal sac wall that envelops a section of the vas deferens to maintain the vas deferens in the operative position; infiltrating the folded portion of the scrotal sac wall and the enveloped section of the vas deferens with an anesthetic injected from a medial port of the hypodermic needle; positioning a surgical clip with opposed medial portions thereof located behind the hypodermic needle and with opposed end portions thereof extending forwardly to terminations protruding beyond the scrotal sac wall; and applying compressive forces to close the surgical clip, thereby clamping the folded portion of the scrotal sac wall together and closing the enveloped vas deferens at two spaced compression points.

In another aspect of the invention, a surgical clip is provided that comprises first and second elongated parts of a like, non-linear configuration; and complementary features carried by the first and second parts in positions to interengage and lock the clip in a clamped condition with respect to a vas deferens and scrotal skin, when the first and second parts are pressed into opposed, mating relation.

In a third aspect, the invention includes a medical device, for administering a local anesthetic during the performance of a vasectomy, that comprises an elongated needle extending from a large diameter end to an acute, scrotal skin-puncturing point; a fitting provided at the large diameter end of the needle for accepting a syringe containing liquid anesthetic; a side-opening injection port formed in the needle at an intermediate location between the large diameter end and the point; and a passage providing fluid communication through the needle from the large diameter end to the injection port, the passage terminating at a location intermediate the injection port and the point.

It is to be understood that both the foregoing general description and the following detailed description are exemplary and explanatory, and are not restrictive of the invention as claimed.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

In the drawings.

Like reference numerals refer to corresponding elements throughout the several views of the drawings.

DETAILED DESCRIPTION OF THE PREFERRED EMBODIMENTS

Figure 1:
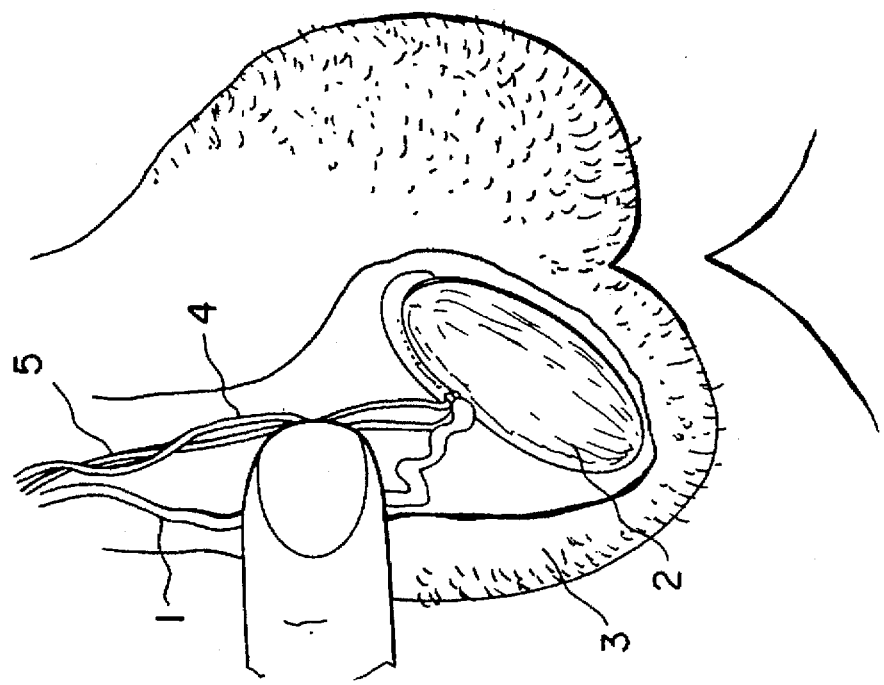
FIG. 1 is a side view of a male genitalia.

FIG. 1 illustrates a portion of the male genitalia, wherein the vas deferens is indicated at 1. The paired testicles 2 contained by scrotal sac 3 are at the ends of the spermatic cord which contain a testicular artery 4 and vein 5. These vessels supply nutrients to the testicles and return metabolic end-products, including hormones, to the general circulation. Sperm produced by the testicles is conveyed upward through the thick, ductular vas deferens 1.

Figure 2:
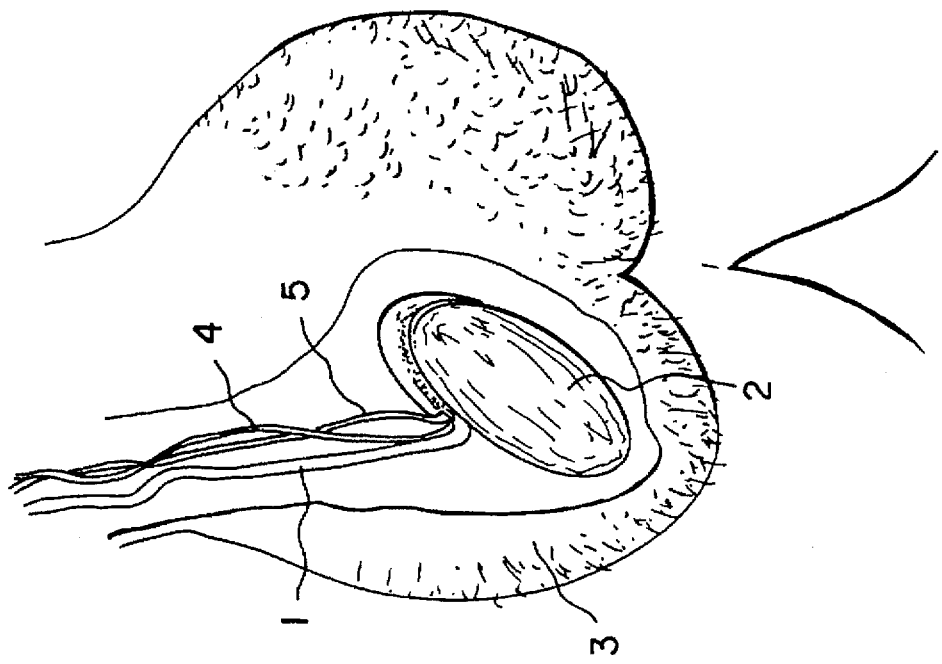
FIG. 2 is a side view of the male genitalia, illustrating the vas deferens manoeuvered to an operative position.
Figure 3:
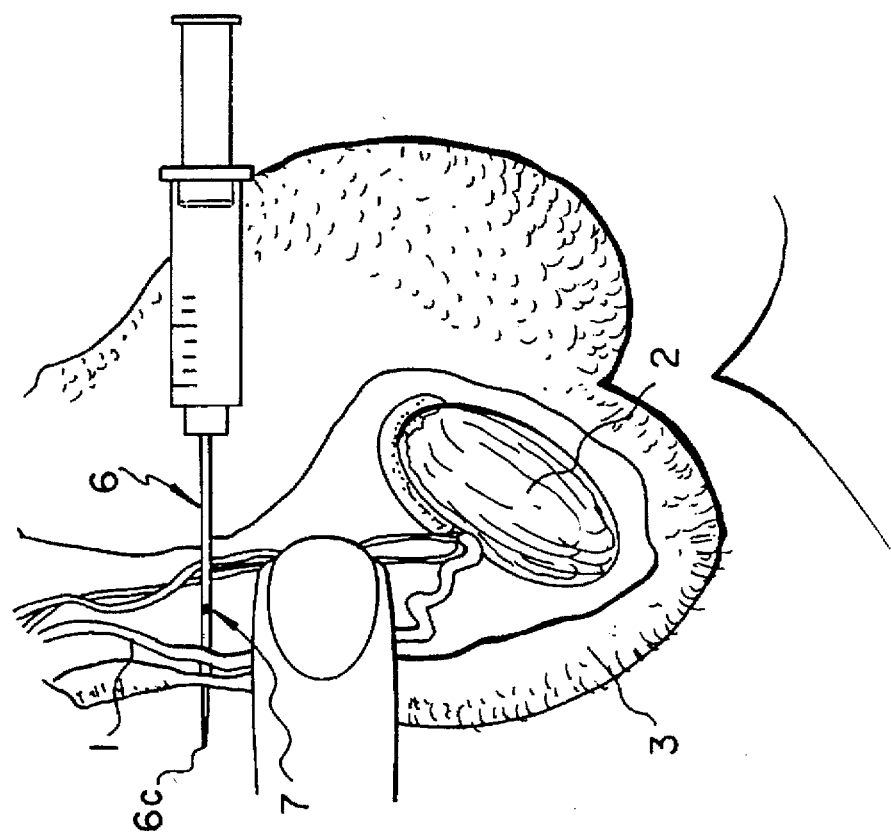
FIG. 3 is a side view of the male genitalia, illustrating the use of a hypodermic needle to maintain the position of the vas deferens and to inject a local anesthetic in accordance with the present invention.

FIG. 2 illustrates the vas deferens 1 being readily identified by digital palpation due to its thickness and then separated from the spermatic cord (artery 4 and vein 5) and manoeuvered forwardly to a frontal, operative position proximate the wall of the scrotal sac 3. Then, as seen in FIG. 3, this operative position of the vas deferens 1 is maintained by passing a hypodermic needle 6 through a folded portion of scrotal sac wall that envelops a section of the drawn out vas deferens. The vas deferens 1 is then isolated in the operative position by the inserted needle 6, safely removed from the spermatic cord. The insertion position of needle 6 is then adjusted such that a side-opening injection port 7 can effectively infiltrate the area surrounding the operative position of the vas deferens 1 with a local anesthetic. The injection port 7 is located at a longitudinal position spaced from the needle point 6c, and the needle 6 is rotated so that infiltration of a generous dermal, subcutaneous area with the local anesthetic is effected.

Figure 4:
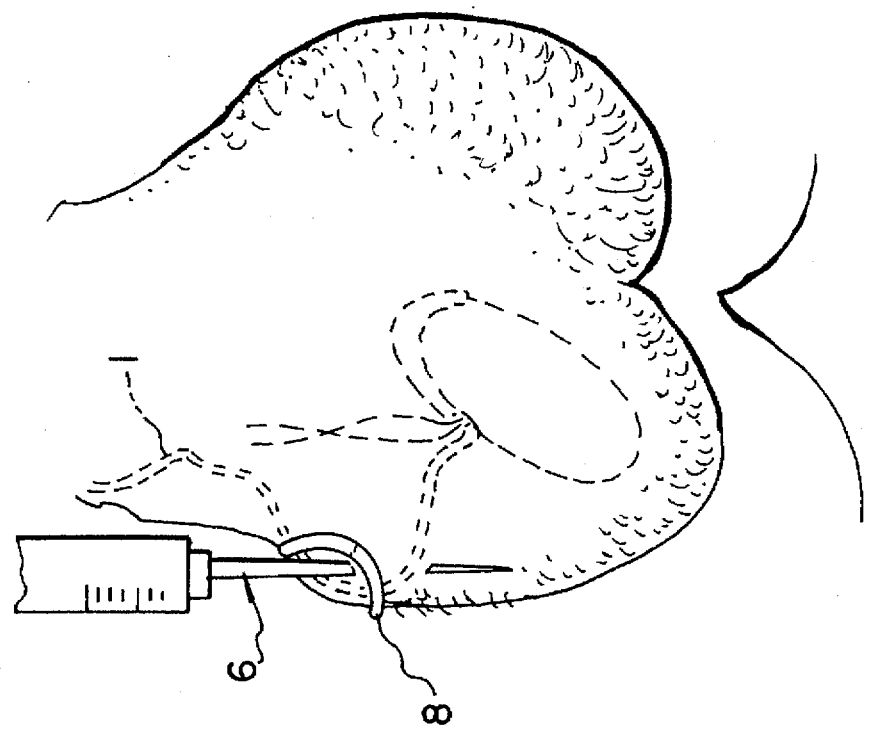
FIG. 4 is a side view of the male genitalia, illustrating the application of a surgical clip to the scrotal sac and the vas deferens.

Turning to FIG. 4, a surgical clip 8 is positioned with opposed medial portions passing behind the inserted needle 6 and opposed end portions extending forwardly to terminations protruding beyond the scrotal sac 3. The clip 8 is then closed, using a suitable appliance (not shown), to tightly clamp together the anesthetized exterior folded portion of the scrotal wall along a non-linear line of compression that intersects and closes the enveloped vas deferens 1 at two spaced compression points.

Figure 5A:
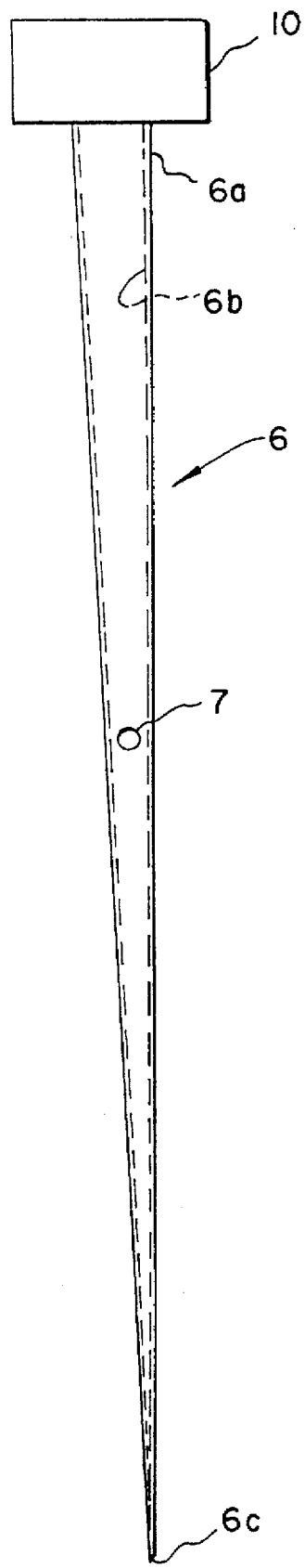
FIG. 5A is an enlarged side view of the hypodermic needle illustrated in FIGS. 3 and 4.
Figure 5B:
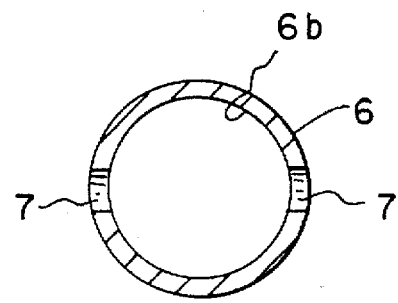
FIGS. 5B and 5C are sectional views of the hypodermic needle of FIG. 5A illustrating alternative injection port arrangements.
Figure 5C:
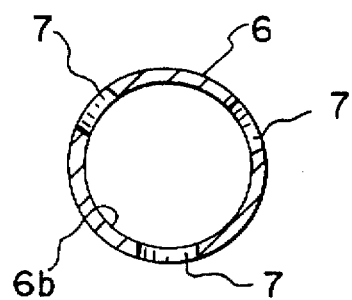

Referring to FIG. 5A, the needle 6 is tapered from a large gauge end 6a, e.g., 18 gauge, that is adapted with a fitting 10, such as a conventional luer lock, that will accept a standard syringe 11 (FIG. 3), to the sharp incision point, 6c, capable of easily penetrating the skin of scrotal sac 3, with minimal patient discomfort. The vas needle 6 has an internal passage 6B extending from end 6a to a location at least beyond where one (FIG. 5A), two (FIG. 5B), or three (FIG. 5C) radial injection openings 7 are positioned to administer the anesthetic when the needle is inserted through the scrotal sac wall to the position shown in FIG. 3.

Figure 6:
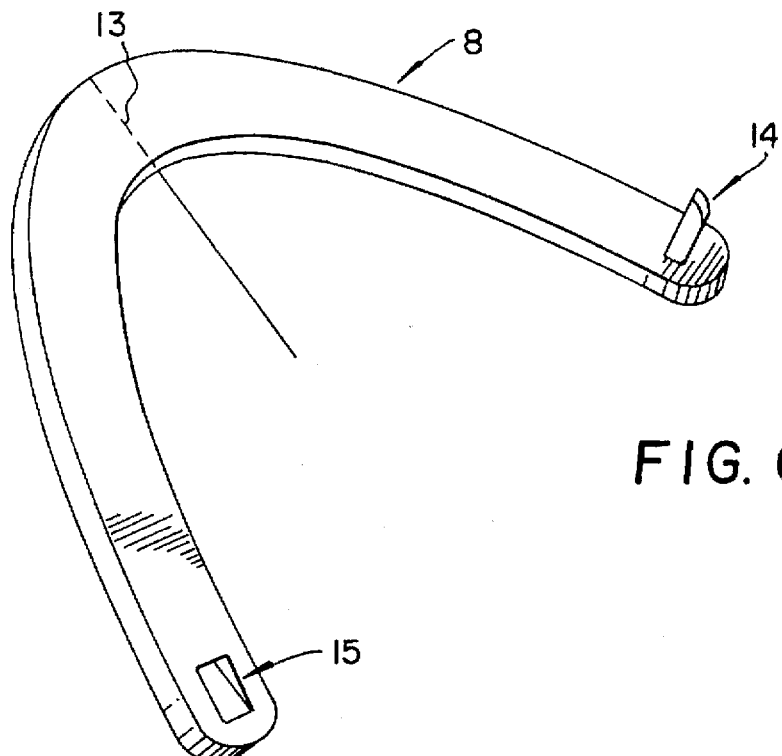
FIG. 6 is an enlarged perspective view of the surgical clip seen in FIG. 4.
Figure 7:
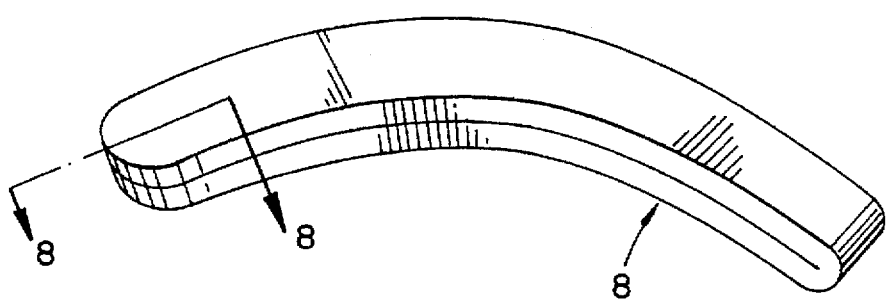
FIG. 7 is a perspective view of the surgical clip of FIG. 6, illustrated in its closed, clamping condition.
Figure 8:
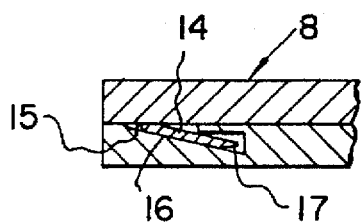
FIG. 8 is a sectional view taken along line 8—8 in FIG. 7.

Turning to FIG. 6, surgical clip 8 is preferably in the shape of a semicircle and consists of deformable material, such as a metal. The clip is preformed at a mid-length location with a hinge section 13, allowing the clip to be forcibly folded on itself into a crescent shape, illustrated in FIG. 7, by a suitable appliance when applied to the anesthetized site of the vasectomy procedure, as illustrated in FIG. 4. To sustain the clip 8 in its closed and clamped condition, one end is provided with a prong 14 and the other end is provided with a recess 15. As seen in FIG. 8, recess 15 is provided with an inclined floor 16 extending into an undercut 17. Thus, when the clip 8 is forcibly folded on itself about hinge section 13, prong 14 is cammed aside into undercut 17, thus locking the clip in its closed, clamped condition, with the folded section of the scrotal skin trapped between the folded sections of the clip and the vas deferens 1 clamped shut at two spaced points.

After the clip 8 has been applied, the isolated tissue section (scrotal skin and vas deferens) may be excised along the frontal edge of the clip using a scalpel or punch biopsy instrument, thus removing a section of the vas deferens. The clip may be left in place for approximately two weeks, then pried open and removed. Alternatively, the tissue section isolated by the vas clip may be simply allowed to necrose and turn to slough. Concurrently, a perimeter of viable scrotal skin along the rear edge of the vas clip heals, and the vas clip then can be removed.

Figure 9A:
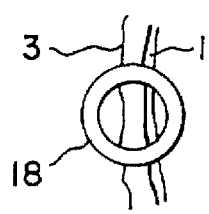
FIGS. 9A and 9B are plan views of alternative surgical clip configurations.
Figure 9B:
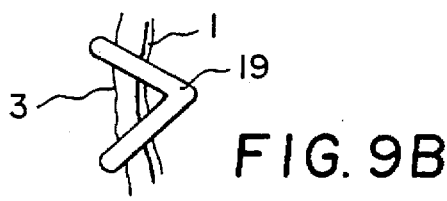

It will be appreciated that the vas clip may take a variety of shaped ranging from circular, as illustrated at 18 in FIG. 9A, to angular, as illustrated at 19 in FIG. 9B.

It will be apparent to those skilled in the art that various modifications and variations can be made in the disclosed surgical procedure and implements (needle and surgical clip) without departing from the scope or spirit of the invention. Other embodiments of the invention will be apparent to those skilled in the art from consideration of the specification and practice of the invention disclosed herein.

It is intended that the specification and examples be considered as exemplary only, with a true scope and spirit of the invention being indicated by the following claims.

What is claimed is:

1. A method of performing a vasectomy, comprising the steps of:

identifying the vas deferens from the spermatic cord by digital palpation;

manoeuvering the vas deferens to an operative position adjacent a wall of the scrotal sac;

inserting a hypodermic needle through a folded portion of the scrotal sac wall that envelops a section of the vas deferens to maintain the vas deferens in the operative position;

infiltrating the folded portion of the scrotal sac wall and the enveloped section of the vas deferens with an anesthetic injected from a medial port of the hypodermic needle;

positioning a surgical clip with opposed medial portions thereof located behind the hypodermic needle and with opposed terminal portions thereof extending forwardly to terminations protruding beyond the scrotal sac wall; and applying compressive forces to close the surgical clip, thereby clamping the folded portion of the scrotal sac wall together and closing the vas deferens at two spaced compression points.

2. The method defined in claim 1, further including the steps of:

withdrawing the hypodermic needle; and excising the portions of the folded scrotal sac wall and the vas deferens located forwardly of the surgical clip.

3. A medical device for administering a local anesthetic during the performance of a vasectomy, comprising:

an elongated needle smoothly tapered from a large diameter end to an acute, scrotal skin-puncturing point;

a fitting provided at the large diameter end of the needle for accepting a syringe containing liquid anesthetic;

a side-opening injection port formed in the needle at an intermediate location between the large diameter end and the point; and a passage providing fluid communication through the needle from the large diameter end to the injection port, the passage terminating at a location intermediate the injection port and the point.

4. The medical device defined in claim 3, wherein a pair of angularly spaced, side-opening injection ports are formed in the needle at the intermediate location.

5. The medical device defined in claim 3, wherein three angularly spaced, side-opening injection ports are formed in the needle at the intermediate location.

6. The medical device defined in claim 3, wherein the large diameter end of the needle is of approximately eighteen gauge.

7. A surgical clip for use in performing a vasectomy, comprising:

first and second elongated parts of like, non-linear configurations and having respective first and second clamp surfaces of uniform lengths;

a hinge section joining the first and second parts at corresponding ends and including a hinge axis about which the first and second parts may be pivoted from a fully open clip condition to a closure clip condition with the first and second clamp surfaces in opposed, substantially uniformly spaced relation along the lengths thereof, a line extension of the hinge axis being symmetrically flanked by the first and second parts along the lengths thereof when in the fully open clip condition, in the fully closed clip condition, the first and second clamp surfaces assuming continuous clamped engagements with scrotal sac skin along a non-linear clamping zone that intersects a vas deferens at two locations spaced along a length thereof; and complementary features carried at free ends of the first and second parts for interengagement to lock the first and second parts in the closure clip condition.

8. The surgical clip defined in claim 7, wherein the first and second parts are each of a crescent shape.

9. The surgical clip defined in claim 7, wherein the first and second parts are each of an angular shape.

* * * * *